(12) United States Patent
Hucke et al.

(10) Patent No.: US 7,855,189 B2
(45) Date of Patent: Dec. 21, 2010

(54) N-PHENYLPHOSPHORIC ACID TRIAMIDES, METHOD FOR THE PRODUCTION THEREOF AND THEIR USE AS AGENTS FOR REGULATING OR INHIBITING ENZYMATIC UREA HYDROLYSIS

(75) Inventors: André Hucke, Reinsdorf (DE); Hans-Joachim Niclas, Berlin (DE); Hartmut Wozniak, Cunnersdorf (DE); Hans-Jürgen Michel, Machern (DE); Carola Schuster, Halle/Saale (DE)

(73) Assignee: SKW Stickstoffwerke Piesteritz GmbH, Lutherstadt Wittenberg (DE)

( * ) Notice: Subject to any disclaimer, the term of this patent is extended or adjusted under 35 U.S.C. 154(b) by 767 days.

(21) Appl. No.: 11/658,157

(22) PCT Filed: Feb. 4, 2005

(86) PCT No.: PCT/EP2005/001157

§ 371 (c)(1),
(2), (4) Date: Feb. 8, 2007

(87) PCT Pub. No.: WO2006/010389

PCT Pub. Date: Feb. 2, 2006

(65) Prior Publication Data

US 2008/0070871 A1    Mar. 20, 2008

(30) Foreign Application Priority Data

Jul. 23, 2004    (DE)    ........................ 10 2004 035 742

(51) Int. Cl.
    *A01N 57/30*    (2006.01)
    *A61K 31/66*    (2006.01)
    *C07F 9/22*    (2006.01)

(52) U.S. Cl. ..................... 514/131; 514/116; 514/119; 514/120; 514/124; 514/130; 564/12; 564/14

(58) Field of Classification Search .................. 514/131, 514/116, 119, 120, 124, 130; 564/12, 14
See application file for complete search history.

(56) References Cited

U.S. PATENT DOCUMENTS 4,242,325 A    12/1980    Bayless et al.
4,517,004 A    5/1985    Swerdloff et al.
6,017,950 A  *    1/2000    Berkowitz et al. .......... 514/460

FOREIGN PATENT DOCUMENTS

EP    0 119 494 A1    9/1984
WO    WO 96/04856    12/1996

* cited by examiner

*Primary Examiner*—Peter G O'Sullivan
(74) *Attorney, Agent, or Firm*—Nixon & Vanderhye P.C.

(57) ABSTRACT

The invention relates to N-phenylphosphoric acid triamides of general formula (I)

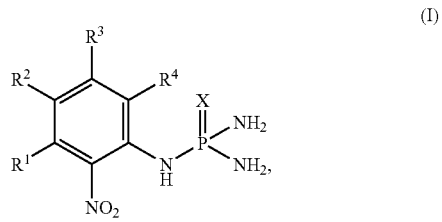

to a method for the production thereof and to their use as agents for regulating or inhibiting enzymatic urea hydrolysis. In formula (I), X represents oxygen or sulfur; $R^1$, $R^2$, $R^3$, $R^4$, $R^5$, independent of one another, represent hydrogen $C_1$-$C_8$ alkyl/heteroalkyl, $C_2$-$C_8$ alkenyl/heteroalkenyl, $C_2$-$C_8$ alkynyl/heteroalkynyl, $C_3$-$C_8$ cycloalkyl/heterocycloalkyl, $C_3$-$C_8$ cycloalkenyl/heterocycloalkenyl, $C_6$-$C_{10}$ aryl/$C_5$-$C_{10}$ heteroaryl, aralkyl, heteroarylalkyl, alkaryl, alkheteroaryl, alkoxy, aryloxy, hetaryloxy, alkylthio, arylthio, hetarylthio, acyl, aroyl, hetaroyl, acyloxy, aroyloxy, hetaroyloxy, alkoxycarbonyl, aryloxycarbonyl, hetaryloxycarbonyl, alkylsulfonyl, fluorine, chlorine, bromine, iodine, cyano, nitro, sulfo, carbonyl, carboxy, carbamoyl, sulfamoyl, with the provision that: at least one radical R is not hydrogen; in the event $R^1$, $R^2$, $R^4$, $R^5$ represent H, $R^3$ is not nitro or cyano, and; in the event $R^1$ represents Cl or $R^1$ and $R^3$ represent Cl, at least one of the remaining radicals is not hydrogen.

17 Claims, No Drawings ns application is the US national phase of international application PCT/EP2005/001157 filed 4 Feb. 2005, which designates the U.S. and claims the benefit of DE 10 2004 035 742.0 filed 23 Jul. 2004, the entire contents of each are hereby incorporated by reference.

N-PHENYLPHOSPHORIC ACID TRIAMIDES, METHOD FOR THE PRODUCTION THEREOF AND THEIR USE AS AGENTS FOR REGULATING OR INHIBITING ENZYMATIC UREA HYDROLYSIS

This application is the US national phase of international application PCT/EP2005/001157 filed 4 Feb. 2005, which designates the U.S. and claims the benefit of DE 10 2004 035 742.0 filed 23 Jul. 2004, the entire contents of each are hereby incorporated by reference.

The present invention relates to novel N-phenyl phosphoric acid triamides, methods for their production, compositions containing them and the use of these N-phenyl phosphoric acid triamides or compositions containing them as means for regulating or inhibiting enzymatic (urease-catalysed) urea hydrolysis (also in combination with means for restricting nitrification) so as to avoid nitrogen losses when using urea-based fertilisers and to reduce the effect of ammonia in animal enclosures as a result of extensive elimination of urea hydrolysis and as an additive to feed urea within the framework of animal nutrition, in particular for ruminants. The invention further relates to fertiliser compositions which contain N-phenyl phosphoric acid triamides and a urea-based fertiliser.

Urea is an originally biogenous metabolite which is split by the urease enzyme into ammonia and carbon dioxide. The reaction takes place exceptionally quickly and effectively, and so is responsible for N-losses when using urea-based fertilisers. These are particularly high if the soil does not have sufficient sorption force in order to bind the ammonia released in the form of ammonium ions. As a result of this agriculture loses considerable quantities of nitrogen each year which thus contribute to environmental pollution, and this means on the other hand that more fertiliser is required.

Moreover, under unfavourable climatic conditions and/or with application onto light soils, high ammonia concentrations can occur spontaneously in the soil which then in addition have a negative impact upon the germination and sprouting of young plants.

Because urea is the nitrogen fertiliser with the greatest percentage N content and is by far the dominant N fertiliser worldwide, the search for practicable solutions for reducing the N losses caused by urease is understandable. In order to fulfil this objective, a plurality of solutions have been proposed. Noteworthy in this context is the acid coating of urea prills or granules so as in this way to be able to trap the ammonia produced by the formation of salt, or coating with substances by means of which the release of urea is slowed down, and so the ammonia produced can be "buffered away" without any problem.

Moreover, the urease-catalysed urea hydrolysis partly causes a significant ammonia presence by splitting the urea found in droppings, and in particular in urine, in animal enclosures which—apart from an unpleasant odour with a correspondingly high concentration—has a negative impact upon the development and growth of the animals.

The N losses from the urease-catalysed hydrolysis of urea and nitrification can be up to 50% under unfavourable conditions, particularly in tropical and subtropical climates. In order to minimise this loss potential, a number of separate fertiliser applications are recommended according to the requirements, which for the farmer, however, are associated with considerable economic disadvantages and corresponding additional expense as a result of additional application costs.

Possibilities for restricting the nitrogen losses are provided by specifically inhibiting the urease-catalysed urea hydrolysis on the one hand and by inhibiting nitrification on the other hand. In the first case, the addition of such substances, which leads to urease inhibition, seems promising, not only the application for fertilisation purposes of course being possible, but also application for minimising the effect of ammonia in animal enclosures or its addition to feed urea.

The use of urease inhibitors is an effective possibility for clearly slowing down enzymatic urea hydrolysis which happens exceptionally quickly under normal conditions. By delaying this enzyme reaction, the undecomposed fertiliser urea can penetrate into lower soil layers.

Ammonia losses are thus almost excluded by the sorption potential of the layers of soil found over these, differently than on the soil surface. Moreover, in this way it is possible to use urea and fertilisers containing urea for light soil locations without any loss.

In animal enclosures, the emission of ammonia from dung and animal excrement can be effectively restricted by the addition of a urease inhibitor.

From the point of view of loss-free and so environmentally friendly storage and application of organic fertilisers such as dung or liquid manure, the use of urease inhibitors, if appropriate also in combination with nitrification inhibitors, is likewise a recommended step for increasing the fertiliser and so fertilisation efficiency of commercial fertilisers.

It is known that especially in the animal feeding of ruminants, supplying the animals with protein-rich and so performance enhancing food is partly a financial problem for the farmer, in some regions of the earth however is also for climatic reasons a problem which can not be solved the whole year round. From today's perspective, the substitution of plant protein with carcass meal in the ruminant feed can not be considered for health policy reasons. In order to overcome this situation, a partial substitution of the high-value protein-rich plant feed of the animals can be offered by so-called "non-protein nitrogen compounds" (NPN compounds). Urea can take on this role if it is possible to control the urease-catalysed urea hydrolysis taking place in the animal rumina such that the ammonia rates released are immediately converted into microbial protein by micro-organisms which are present, and consequently can not trigger any toxic effects. The use of suitable urease inhibitors is also possible here.

It is known from the literature that certain organic, but also inorganic compounds can inhibit the urease-catalysed urea hydrolysis (see S. Kiss, M. Simihäian, Improving Efficiency of Urea Fertilizers by Inhibition of Soil Urease Activity, Kluwer Academic Publishers (2002)).

With the discovery of phosphoric acid ester diamides (DD 122 177), compounds were found which are exceptionally effective urease inhibitors. Similarly effective is a series of derivatives of the phosphoric acid triamide, including the base element (see e.g. U.S. Pat. No. 4,540,428, 4,676,822, 4,696,693, 4,537,614, 4,517,004, EP 0 119 487), of which the N-(n-butyl)thiophosphoric acid triamide (NBTPT) was previously commercialised as the only representative (IMC AGRICO Corp., product name Agrotain®).

Upon close examination of these substances it becomes clear that several are relatively susceptible to hydrolysis due to which in particular their effective life and so their applicability is considerably restricted. On the other hand, they can partly only be obtained with a low rate of yield or by means of expensive production methods such that the economics are not justifiable. Due to the susceptibility to hydrolysis of the NBTPT and its instability in combination with urea-based fertilisers, this active substance is used as a liquid formulation, the formulation being mixed with the urea-based fertiliser directly before the fertiliser application, and this is exceptionally uneconomical. An even distribution of the active substance over the fertiliser granules can hardly be guaranteed here. Moreover, NBTPT fails under anaerobic conditions in rice cultivation, i.e. precisely where the highest nitrogen losses and ammonia emissions are recorded, because the formation of the NBTPT oxygen analogue, and so of the actual urease inhibitor, is not possible or only possible slowly (see *Fertilizer Research* 42, 251 (1995)).

A further disadvantage influencing the use of the aforementioned compounds is that they have different migration characteristics than urea. The inhibitor is thereby separated from the urea substrate, and this can have a negative impact upon the enzyme inhibition. However, it is also possible for originally effective urease inhibitors to lose their inhibiting effect when they come into contact with the soil due to reaction with the soil components or fixation.

As well as the N losses due to uncontrolled urease-catalysed hydrolysis of the urea, nitrogen is lost in the form of nitrate which is withdrawn from the plant feed being washed out or displaced into deeper soil layers. Moreover, these N losses can be further increased if during the rapid nitrification of ammonium ions, relatively large quantities of nitrate are formed which can themselves be converted into molecular nitrogen by incipient denitrification, and so are likewise no longer available for the plant nutrition.

Suggested as nitrification inhibitors are, for example, substituted pyrazols (DD 131 063, U.S. Pat. No. 3,635,690), triazols (DE-OS 18 04 994, U.S. Pat. No. 3,697,244, 3,701, 645), as are also active substance combinations based upon pyrazol compounds and dicyandiamide (DD 227 957) or upon triazol derivatives and dicyandiamide (WO 95/22 515). Furthermore, in U.S. Pat. No. 5,364,438 novel liquid nitrogen fertilisers are described which, as well as dissolved nitrogen in the form of urea and other nitrogen feed forms, also contain portions of N-(n-butyl)thiophosphoric acid triamide (NBTPT) and dicyandiamide (DCD).

For the broad minimisation of nitrogen losses when using urea-based fertilisers, it is possible to use urease inhibitors in combination with nitrification inhibitors. Investigations into this have shown, however, that urease and nitrification inhibitors can not be combined with one another in any way because, under certain conditions, the use of a nitrification inhibitor in addition to the urease inhibitor can have a negative effect upon the intended reduction in ammonia losses (NBTPT/DCD: *Biol. Fertil. Soils* 36 129 (2002)). This finding is also reflected in the yields which partly lay on the level of the single urea fertiliser used as a comparison (NBTPT/Carbide: *Biol. Fertil. Soils* 22, 89 (1996)).

Therefore, the object which formed the basis of the present invention was to make available such types of urease inhibitors for practical use which, when used with fertilising urea or other urea-based fertilisers, are capable of restricting the enzyme-catalysed urea hydrolysis to such a degree that nitrogen losses resulting from this in the form of ammonia are almost excluded and that the presence of ammonia in animal enclosures due to the spontaneous decomposition of the urea is clearly reduced. It should be possible to combine the novel urease inhibitors with nitrification inhibitors without any loss of effect so as to achieve further improvement of the N exploitation in urea-based fertilisers.

Likewise, these urease inhibitors should slow down the splitting of urea taking place in the rumen of ruminants when using urea within the framework of animal feeding such that the animals are not subjected to any harm due to ammonia intoxication which otherwise may occur, and on the other hand are able to make use of the nitrogen made available in this way for the body-specific protein biosynthesis.

A further field of application is medicine. Urease inhibitors can be used for the prophylaxis or therapy of dysfunctions or diseases which are directly or indirectly induced or promoted by urease activity. Examples of this are catheter encrustation, inflamed and ulcerous stomach and bowel diseases, urolithiasis, pyelonephritis, nephrolithiasis, ammonia encephalopathy, hepatic encephalopathy, hepatic coma, infections of the urinary passage and gastrointestinal infections. These can be caused, for example, by urease-producing microorganisms such as *helicobacter pylori*.

These objects are fulfilled according to the invention by the provision and use of the N-phenyl phosphoric acid triamides with the structures defined in Claim 1.

It has been shown, surprisingly, that with appropriate substitution on the phenyl moiety, the N-phenyl phosphoric acid triamides provided and used according to the invention are highly effective urease inhibitors with exceptionally long-lasting effect. As well as sufficient resistance to hydrolysis, the N-phenyl phosphoric acid triamides according to the invention can also be produced from simple raw materials without any technical problems and cost-effectively. Moreover, the N-phenyl phosphoric acid triamides according to the invention can be easily incorporated into urea or urea-based fertilisers using conventional methods, efficient application together with the fertiliser or ruminant feed being possible. They are both sufficiently soluble in water and easily soluble in oil, and this could not be foreseen either. A further advantage of the N-phenyl phosphoric acid triamides according to the invention is their problem-free combinability with nitrification inhibitors.

The invention further relates to methods for producing the N-phenyl phosphoric acid triamides according to the invention as defined in Claim 5, compositions which contain these N-phenyl phosphoric acid triadiamides as defined in Claim 6, a fertiliser composition as defined in Claim 9, and the uses defined in Claims 12 to 17.

Further advantageous and/or preferred embodiments of the invention are the subject matter of the sub-claims.

The N-phenyl phosphoric acid triamides according to the invention as urease inhibitors have the general formula (I):

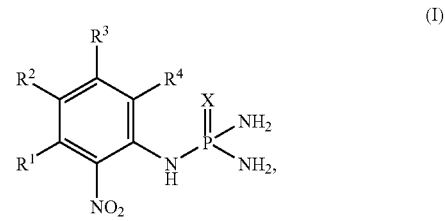

in which:
X represents oxygen or sulphur;
$R^1$, $R^2$, $R^3$, $R^4$, $R^5$ represent the following, independently of one another: hydrogen, $C_1$-$C_8$-alkyl/heteroalkyl, $C_2$-$C_8$-alkenyl/heteroalkenyl, $C_2$-$C_8$-alkinyl/heteroalkinyl, $C_3$-$C_8$-cycloalkyl/heterocycloalkyl, $C_3$-$C_8$-cycloalkenyl/heterocycloalkenyl, $C_6$-$C_{10}$-aryl/$C_5$-$C_{10}$-heteroaryl, aralkyl, heteroarylalkyl, alkaryl, alkheteroaryl, alkoxy, aryloxy, hetaryloxy, alkylthio, arylthio, hetarylthio, acyl, aroyl, hetaroyl, acyloxy, aroyloxy, hetaroyloxy, alkoxycarbonyl, aryloxycarbonyl, hetaryloxycarbonyl, alkylsulfonyl, fluorine, chlorine, bromine, iodine, cyano, nitro, sulfo, carbonyl, carboxy, carbamoyl, sulfamoyl, provided that at least one moiety R is different to hydrogen, that in the case of $R^1$, $R^2$, $R^4$, $R^5$=H, $R^3$ is different to nitro or cyano, and that in the case of $R^1$=Cl or $R^1$, $R^3$=Cl, at least one of the remaining moieties is different to hydrogen.

If appropriate, the $R^1$-$R^5$ residues can be substituted in their own right and independently from one another by one or more of the aforementioned groups as well as by amino, alkylamino, dialkylamino, hydroxy or mercapto. Two adjacent moieties R (e.g. $R^1$ and $R^2$) can be connected to one another by means of an alkylene or alkenylene chain by forming a 5-6 membered, if appropriate aromatic ring system which, if appropriate, can contain one or more heteroatoms such as oxygen, nitrogen or sulphur, and can be substituted by the aforementioned groups.

One preferred N-phenyl phosphoric acid triamide of the present invention corresponds to formula (II):

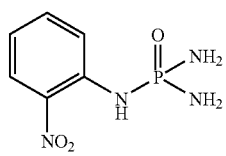

(II)

Moreover, the invention includes salts, tautomers and metal complexes of compounds with the general formula (I) or II) which have a urease-inhibiting effect.

Of course, the person skilled in the art will select the moieties or groups specified in general formula (I) such that no impossible molecules are formed, e.g. chemically or sterically impossible molecules.

The alkyl, alkenyl or alkinyl groups mentioned in the following, with the corresponding carbon number, can be straight-chained or branched, and singly or multiply unsaturated.

In the following, in order to avoid unnecessary redundancy and also at times for the sake of simplicity, only the terms "alkyl group", "heteroalkyl group" or "cycloalkyl group" etc. will be used, but the corresponding unsaturated groups are to be respectively included. It is clear to the person skilled in the art that alkenyl or alkinyl groups must have at least 2 carbon atoms and cyclic hydrocarbon groups at least 3 carbon atoms.

The term "alkyl" relates, in any combination with any other groups, in particular to an alkyl group which has 1 to 8 carbon atoms, e.g. a methyl, ethyl, n-propyl, isopropyl, n-butyl, isobutyl, tert-butyl, amyl, isoamyl, n-hexyl, 2,2-dimethylbutyl or n-octyl group.

The term "alkenyl" relates, in any combination with any other groups, in particular to an alkenyl group which has 2 to 8 carbon atoms, e.g. an ethenyl, n-propenyl, isopropenyl, n-butenyl, isobutenyl, tert-butenyl, n-hexenyl, 2,2-dimethylbutenyl, n-octenyl, allyl, isoprenyl or hex-2-enyl group.

The term "alkinyl" relates, in any combination with any other groups, in particular to an alkinyl group which has 2 to 8 carbon atoms, e.g. an ethinyl, n-propinyl, isopropinyl, n-butinyl, isobutinyl, tert-butinyl, n-hexinyl, 2,2-dimethylbutinyl or n-octinyl group.

The term "heteroalkyl" relates with regard to the alkyl part to an above-defined alkyl group, but should also include an appropriate heteroalkenyl or heteroalkinyl group in which one or more carbon atoms are replaced by at least one oxygen, nitrogen, phosphor or sulphur atom.

It is clear that all of the groups defined above can be substituted by themselves or other of the groups defined above provided the urease-inhibiting effect is maintained.

The term "aryl" relates to an aromatic cyclic group which has one or more rings and is formed by a structure which contains 6 to 10 ring carbon atoms. Of course, in the case of several rings, one or more rings can be fully or partially hydrogenated (an example of this is the 1,2,3,4,-tetrahydro-naphthalene-1-yl group). Moreover, an aryl group can be substituted by alkyl or heteroalkyl groups (each defined as above). Examples are a phenyl, naphthyl, indene, 2-, 3- or 4-methoxyphenyl, 2-, 3- or 4-ethoxyphenyl, 4-carboxyphenylalkyl or 4-hydroxyphenyl group.

The terms "aralkyl" and "heteroarylalkyl", respectively, relate to groups which, according to the above and following definitions, include both aryl and heteroaryl (defined below) and alkyl and/or heteroalkyl (and also the corresponding alkylene/heteroalkylene and alkinyl/heteroalkinyl groups) and/or carbocyclic groups (defined below) and/or heterocycloalkyl ring systems (defined below), e.g. a tetrahydroisochinolinyl, benyzl, 2- or 3-ethylindolyl or 4-methylpyridino group.

In order to avoid unnecessary redundancy, the terms "aralkyl" and "heteroarylalkyl" should also include the terms "alkaryl" and "alkheteroaryl".

The terms "cycloalkyl" and "carbocyclic" relate to a saturated or partially unsaturated, cyclic, and if appropriate branched group, which has one or more rings which form a structure which contains 3 to 8 carbon atoms, e.g. a cyclopropyl, cyclobutyl, cyclopentyl, cyclohexyl, tetralin, cyclopentenyl or cyclohex-2-enyl group.

The term "heterocycloalkyl" relates to the cycloalkyl and carbocylic groups, respectively, defined above, in which one or more carbon atoms are replaced by one or more oxygen, nitrogen, phosphor or sulphur atoms. Specific examples are aziridin, furan, pyrrolidin, piperidin, morpholin, oxazolidin, thiazolidin, N-methylpiperazino or N-phenylpiperazin groups.

The term "heteroaryl" relates to an aryl group with 5 to 10 ring atoms in which one or more carbon atoms are replaced by an oxygen, nitrogen, phosphor or sulphur atom. Examples are pyrrol, furan, thiophen, pyrazol, isoxazol, isothiazol, imidazol, oxazol, thiazol, 1,2,4-triazol, 1,2,4-oxadiazol, 1,2,4-thiadiazol, 1,3,4-oxadiazol, 1,3,4-thiadiazol, 1,2,5-oxadiazol, 1,2,5-thiadiazol, tetrazol, pyridin, pyridazin, pyrimidin, pyrazin, 1,2,3-triazin, 1,2,4-triazin, 1,3,5-triazin and indole groups.

It is once again pointed out that all of the groups defined above can be substituted both with themselves and also with other groups defined above provided the urease-inhibiting effect is maintained.

The compounds I according to the invention are accessible by means of analogous application of known methods (Chem. Ber. 26, 2937 (1893); J. Chem. Soc. 81, 1362 (1902); Z. Obsc. Chim. 30, 4048 (1960)), X, $R^1$-$R^5$ having the significance described above. Preferably, the N-phenyl phosphoric acid triamides are produced in a way such that one $a_1$) converts anilines or hydrochlorides of the same with phosphoryl chloride (POCl$_3$) or thiophosphoryl chloride (PSCl$_3$), if appropriate in the presence of an organic solvent and a tertiary base, at temperatures from 0 to 150° C., if appropriate in an inert gas atmosphere, according to equation (1) into N-phenyl phosphoric acid amide dichlorides of type (A), whereby it is alternatively also possible to obtain compounds (A) with X=S by sulphurising the corresponding oxygen derivatives,

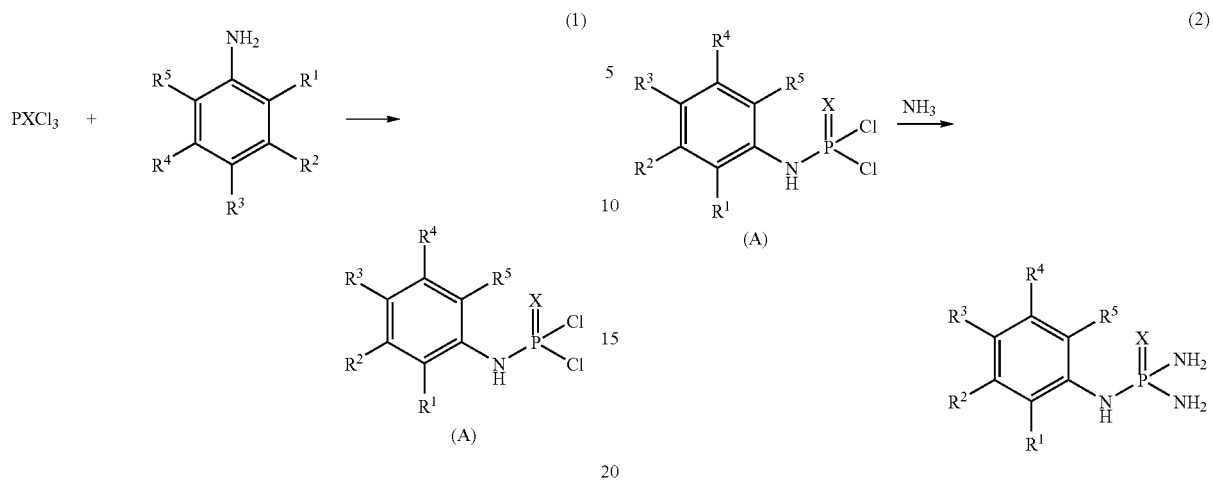

a₂) allows phosphorpentachloride (PCl₅) to react with an aniline, in an approximately equimolar ratio, if appropriate in an inert organic solvent and if appropriate under an inert gas atmosphere at from 0 to 150° C. according to equation (2) to form compounds of type (B) which, if appropriate without any further isolation, are converted with an approximately equimolar quantity of formic acid or water into N-phenyl phosphoric acid amide dichlorides of type (A), whereby it is possible to obtain compounds (A) with X=S by means of sulphurisation of the corresponding oxygen derivatives,

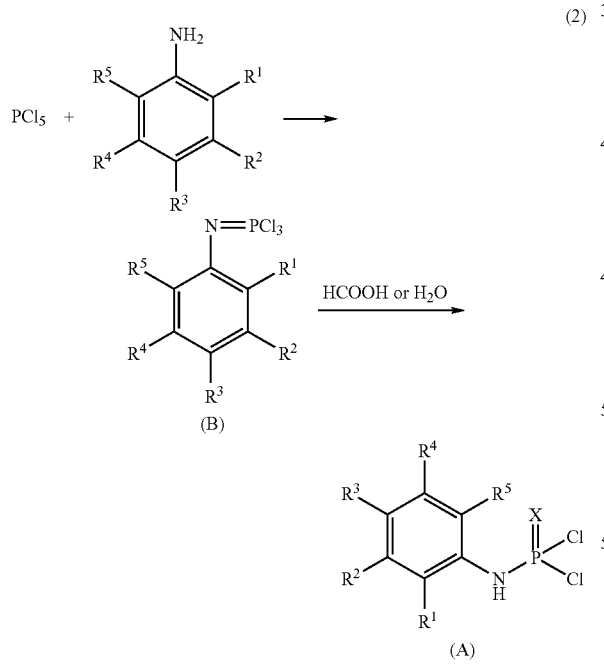

and then b) allows the type (A) compounds formed in step a₁) or a₂) to react with ammonia, if appropriate in an inert organic solvent, at temperatures of from −80 to 30° C. according to equation (2) so as to form the desired end product:

With appropriate substitution on the phenyl moiety, the N-phenyl phosphoric acid triamides according to the invention, or compositions containing these, have an exceptional inhibition effect for practical purposes, by means of which they can slow down or temporarily stop the enzymatic urea hydrolysis such that ammonia losses within the framework of fertilising measures when using organic and/or mineral nitrogen fertilisers containing urea are reduced to a minimum or the occurrence of harmful or troublesome ammonia concentrations in animal husbandry are eliminated, for example by breaking down urea in animal excrement or by breaking down feed urea in the rumina within the framework of ruminant nutrition.

It is immaterial here whether the effect of the N-phenyl phosphoric acid triamides according to the invention or compositions containing these extends to fertilisation measures or to preventative measures for avoiding high concentrations of ammonia in animal enclosures or is applied to the use of feed urea within the framework of ruminant nutrition.

The compounds according to the invention are preferably used together with urea-based fertilisers, preferably in a quantity of from 0.001 to 10% by weight in relation to the weight of the urea-based fertiliser, or added to the feed urea or to the animal excrement in animal enclosures. It is insignificant here within the framework of fertilisation measures, for example, whether they are first applied over the surface of the fertilizer, incorporated into it or are applied together with or separately from the fertilisers containing urea within a justifiable time span.

The subject matter of the invention therefore also includes compositions which include the N-phenyl phosphoric acid triamides used according to the invention and a urea-based mineral and/or organic fertiliser.

The compounds proposed by the invention in the way described above can be combined, for example, in a quantity of from 0.01 to 10% by weight in relation to the weight of the urea-based fertiliser with one or more of the following compounds, which are nitrification inhibitors, in order at the same time to prevent and restrict, respectively, urease-catalysed urea hydrolysis and nitrification:

a) Pyrazol derivatives with the general formula (IV), or salts or complex compounds thereof:

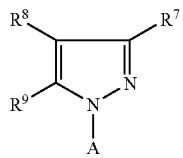
(IV)

in which

R$^7$, R$^8$, R$^9$ represent, independently of one another, hydrogen, halogen, C$_1$-C$_8$-alkyl, or C$_3$-C$_8$-cycloalkyl and A the moiety H
or the moiety

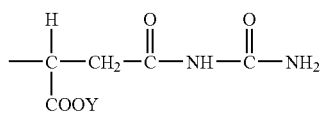

with Y=H, Na, K, NH$_4$
or the moiety
—CH$_2$—B with B=(di)alkylamino

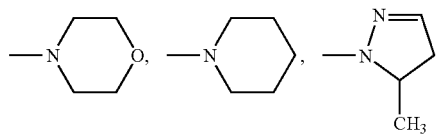

or the moiety

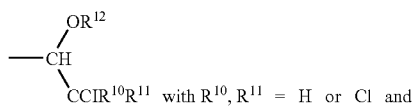 with R$^{10}$, R$^{11}$ = H or Cl and

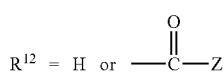

with Z=C$_1$-C$_8$-alkoxy, C$_1$-C$_8$-alkylamino, C$_6$-C$_{10}$-arylamino
or the moiety

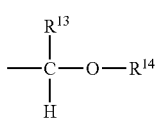

with R$^{13}$, R$^{14}$=H, C$_1$-C$_8$-alkyl, C$_7$-C$_{18}$-alkylaryl, C$_6$-C$_{10}$-aryl or the moieties

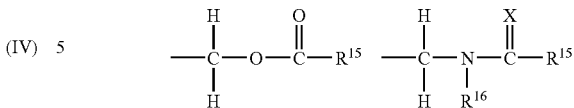

with R$^{15}$=C$_1$-C$_{20}$-alkyl, C$_3$-C$_8$-cycloalkyl, C$_6$-C$_{10}$-aryl or alkylaryl from C$_1$-C$_4$-alkyl and C$_6$-C$_{10}$-aryl groups; with X=oxygen or sulphur and with R$^{16}$=C$_1$-C$_4$-alkyl, C$_3$-C$_8$-cycloalkyl, C$_6$-C$_{10}$-aryl or H, wherein the alkyl and aryl moieties listed can be substituted with themselves or by C$_1$-C$_4$-alkylsulfonyl, C$_1$-C$_4$-alkoxy, C$_1$-C$_4$-acyl, halogen, hydroxyl, trimethylsilyl, amino, nitro, cyano, carbonyl, carboxyl or C$_1$-C$_5$-carboxyalkyl.

b) 1H-1,2,4-triazoles or their salts or complex compounds, c) dicyandiamide.

For use as urease inhibitors, for example in order to reduce nitrogen losses when fertilising with fertiliser urea or urea-based fertilisers, or in order to reduce the ammonia presence due to the dung or animal excrement in animal enclosures, or in order to avoid toxic effects when using feed urea, the suitable compounds according to the invention can be produced and applied in different ways.

The compounds according to the invention can be incorporated into the urea or into the fertilisers containing urea before or during the granulation from the fused phase. Furthermore, they can be applied to the surface of the urea or fertiliser granules or added to liquid fertilisers containing urea. Finally, the addition of urease inhibitors to organic fertilisers containing urea, such as dung or liquid manure is possible. Moreover, in addition to applying urea-based fertilisers, the compounds according to the invention can also in a preliminary or subsequent step be applied to the field separately. The compounds according to the invention can be used here in pure form, as a powder-type material, as pellets or liquefied material, an aqueous solution or as a special formulation, added with the conventional excipients, carriers and diluters known to the person skilled in the art, or a combination of these means. It is immaterial here whether the effective content substance is formulated in liquid form as e.g. a solution, emulsion or suspension, or in solid form as a dustable or dispersable powder. Wettable powders, emulsifiable concentrates and suspension concentrates generally, but not necessarily, contain surface-active means, e.g. a wetting, dispersion, emulsification or suspension means. The respective formulation methods correspond to the prior art, and are known to the person skilled in the art.

The compounds, compositions and fertilisers according to the invention can, for example, be used with and for fertigation. Fertigation is understood to mean the specific supply of nutrients with irrigation water that can be applied e.g. by drip irrigation, spraying or sprinkling. The plants only receive the quantity of water required for optimal growth so that there is no excess water. Due to lack of vertical water movement in the soil beneath the root penetration zone, nutrient washout losses hardly occur at all. Drip irrigation, spraying or sprinkling with urea inhibitors can take place, for example, after fertilisation or at the same time as the fertilisation. Of course there is no restriction to aqueous solutions or other formulations. For example, sprayable suspensions of fine particles can be used. In this respect, reference is made for example to EP 1 378 499 and WO2004/013253.

The present invention will now be described by means of the following examples, without any restriction, and so purely as an illustration.

EXAMPLES

Example 1

N-(2-nitrophenyl)phosphoric acid triamide

In a 100 ml flask with a reflex condenser and a drying pipe, 4.14 g (0.03 mol) 2-nitroaniline and 6.25 g (0.03 mol) phosphor pentachloride are suspended in 50 ml toluene and heated to boiling point while stirring for 4 hrs. After cooling to 80° C., 1.38 g (0.03 mol) formic acid are slowly added. This is left to cool to room temperature, the solvent is drawn off in a vacuum and the residue is washed with petrol ether. The remaining oil is taken up without any further purification in 50 ml chloroform, and dripped to a solution of approx. 30 ml liquid ammonia in 50 ml chloroform, eliminating all humidity, at from −50 to −30° C., while stirring. The excess ammonia is then left to evaporate overnight at room temperature. The raw product containing ammonium chloride is drawn off and either decocted with diethylamine in chloroform or washed with a little water so as to remove the ammonium chloride. One obtains 3.6 g (55%) N-(2-nitrophenyl)phosphoric acid triamide melting point: approx. 200° C. (disintegration)

$^1$H-NMR (DMSO-$d_6$): δ [ppm]=4.54 (s, 4H, $NH_2$); 6.96 (t, 1H, CH); 7.60 (t, 1H, CH); 7.93 (d, 1H, CH); 8.11 (d, 1H, CH); 8.34 (d, 1H NH)

$^{13}$C-NMR (DMSO-$d_6$): δ [ppm]=118.8; 119.9 (d); 125.6; 133.9 (d); 135.6; 140.7 (d)

$^{31}$P-NMR (DMSO-$d_6$): δ [ppm]=8.8

Example 2

N-(3-methylphenyl)phosphoric acid triamide

In a 100 ml flask with a reflux condenser and drying pipe, 14.3 g (0.1 mol) o-toluidine hydrochloride and 15.3 g (0.1 mol) phosphoryl chloride are suspended in 50 ml toluene and heated to boiling point while stirring for 4 hrs. After cooling the solvent is drawn off from the resulting solution in a vacuum, and the residue is washed with petrol ether. The remaining oil is taken up without any farther purification in 50 ml chloroform, and dripped to a solution of approx. 70 ml liquid ammonia in 100 ml chloroform, eliminating all humidity, at from −50 to −30° C., while stirring. The excess ammonia is then left to evaporate overnight at room temperature. The raw product containing ammonium chloride is drawn off, and either decocted with diethylamine in chloroform or washed with a little water so as to remove the ammonium chloride. One obtains 9.1 g (49%) N-(3-methylphenyl)phosphoric acid triamide.

Melting point: 159-162° C.

$^1$H-NMR (DMSO-$d_6$): δ [ppm]=2.18 (s, 3H, $CH_3$); 3.9 (d, 4H, $NH_2$); 6.52 (d, 1H, NH); 6.81 (d, 1H, CH); 6.87-6.99 (m, 3H, CH)

$^{13}$C-NMR (DMSO-$d_6$): δ [ppm]=21.3 ($CH_3$); 114.3 (d); 117.5 (d); 119.4; 128.2 (d); 137.3; 143.4

$^{31}$P-NMR (DMSO-$d_6$): δ [ppm]=11.6 (m)

Example 3

N-(4-methyl-2-nitrophenyl)phosphoric acid triamide

In a 200 ml flask with a reflux condenser and a drying pipe, 11.3 g (0.06 mol) 4-methyl-2-nitroaniline-hydrochloride are suspended in 100 ml phosphoryl chloride and heated to boiling point while stirring for 4 hours. One then proceeds in the same way as for Example 2. One obtains 4.9 g (35%) N-(4-methyl-2-nitrophenyl)phosphoric acid triamide.

Melting point: >180° C. (disintegration)

$^1$H-NMR (DMSO-$d_6$): δ [ppm]=2.28 (s, 3H $CH_3$); 4.50 (d, 4H, $NH_2$); 7.43 (d, 1H, CH); 7.84 (d, 1H, CH); 7.91 (s, 1H, CH); 8.25 (d, 1H, NH)

$^{13}$C-NMR (DMSO-$d_6$): δ [ppm]=19.2 ($CH_3$); 119.5; 124.3; 127.8; 133.2 (d); 136.5; 138.2 (d)

$^{31}$P-NMR (DMSO-$d_6$): δ [ppm]=8.9

Example 4

Testing for Urease-Inhibiting Effect 30 g soil set to 40% of the maximum water capacity are added with 1 ml urea solution corresponding to 50 mg urea. At the same time the active substance is applied, preferably dissolved in the urea solution. The concentration details for the individual tested active substances given in the following table relate to the quantity of carbamide nitrogen used in the test. The soil, on the surface of which the urea solution (with and without the active substance) is applied is located in an airtight sealed container into which a receiver is inserted at the same time which collects the ammonia released from the urea as ammonium. By rinsing the receiver daily and analysing the $NH_4$—N quantities contained, the $NH_3$—N-release from the urea is determined.

From the summation of the ammonium quantities in the receiver, the percentage inhibition of the urea hydrolysis dependently upon time is calculated and from these values the $t_{50}$ value is determined mathematically.

The $t_{50}$ value is understood to be the time in days since the start of the test at which the urea hydrolysis inhibition is still 50%.

Table 1 gives an overview of the inhibition data for several selected compounds according to the invention determined by this method.

TABLE 1 urease inhibition ($t_{50}$ value) after days by N-phenyl phosphoric acid triamide with the general formula (I)

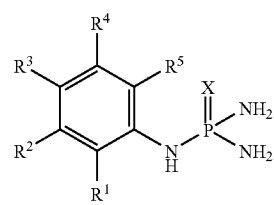

(I)

| compound No. | | conc.[a] % HS-N-related | $t_{50}$ value (d) |
|---|---|---|---|
| 1 | $R^1$ = $NO_2$; $R^2$, $R^3$, $R^4$, $R^5$ = H | 0.05 | >25[b] |
| 2 | $R^2$ = $CH_3$; $R^1$, $R^3$, $R^4$, $R^5$ = H | 0.5 | 11.2 |

[a] conc. % HS-N-related: concentration in % in relation to the quantity of urea nitrogen used
[b] after 25 days still 70% inhibition

The invention claimed is:

1. N-(2-nitrophenyl)phosphoric acid triamides with the general formula (I):

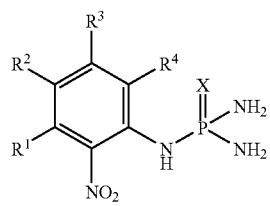

wherein:

X represents oxygen or sulphur $R^1$, $R^2$, $R^3$, $R^4$, $R^5$ represent the following, independently of one another: hydrogen, $C_1$-$C_8$-alkyl/heteroalkyl, $C_2$-$C_8$-alkenyl/heteroalkenyl, $C_2$-$C_8$-alkinyl/heteroalkinyl, $C_3$-$C_8$-cycloalkyl/heterocycloalkyl, $C_3$-$C_8$-cycloalkenyl/heterocycloalkenyl, $C_6$-$C_{10}$-aryl/$C_5$-$C_{10}$-heteroaryl, aralkyl, heteroarylalkyl, alkaryl, alkheteroaryl, alkoxy, aryloxy, hetaryloxy, alkylthio, arylthio, hetarylthio, acyl, aroyl, hetaroyl, acyloxy, aroyloxy, hetaroyloxy, alkoxycarbonyl, aryloxycarbonyl, hetaryloxycarbonyl, alkylsulfonyl, fluorine, chlorine, bromine, iodine, cyano, nitro, sulfo, carbonyl, carboxy, carbamoyl, sulfamoyl, it being possible for two adjacent moieties R to be connected to one another by means of an alkylene or alkenylene chain by forming a 5-6 membered, if appropriate aromatic ring system which, if appropriate, can contain one or more heteroatoms such as oxygen, nitrogen or sulphur, it being possible, if appropriate, for the $R^1$-$R^4$ moieties to be substituted in their own right and independently from one another by one or more of the aforementioned groups as well as by amino, alkylamino, dialkylamino, hydroxy or mercapto, and salts, tautomers and metal complexes of compounds with the general formula (I).

2. N-(2-nitrophenyl)phosphoric acid triamide according to claim 1, wherein formula (I) X=O and $R^1$=$R^2$=$R^3$=$R^4$=H.

3. A method for producing N-(2-nitrophenyl)phosphoric acid triamides according to claim 1, wherein $a_1$) 2-nitroanilines or hydrochlorides of the same are converted with phosphoryl chloride ($POCl_3$) or thiophosphoryl chloride ($PSCl_3$), if appropriate in the presence of an organic solvent and a tertiary base, at temperatures of from 0 to 150° C., if appropriate in an inert gas atmosphere, according to equation (1) into N-(2-nitrophenyl) phosphoric acid amide dichlorides of type (A), whereby it is also alternatively possible to obtain compounds (A) with X=S by sulphurizing the corresponding oxygen derivatives,

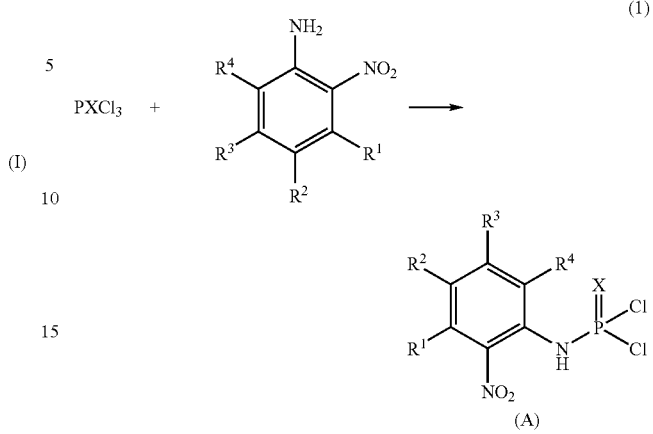

or $a_2$) phosphor pentachloride ($PCl_5$) is allowed to react with a 2-nitroaniline, in an approximately equimolar ratio, if appropriate in an inert organic solvent, and if appropriate under an inert gas atmosphere at from 0 to 150° C. according to equation (2) to form compounds of type (B) which, if appropriate without any further isolation, are converted with an approximately equimolar quantity of formic acid or water into N-(2-nitrophenyl)phosphoric acid amide dichlorides of type (A), whereby it is possible to obtain compounds (A) with X=S by means of sulphurization of the corresponding oxygen derivatives,

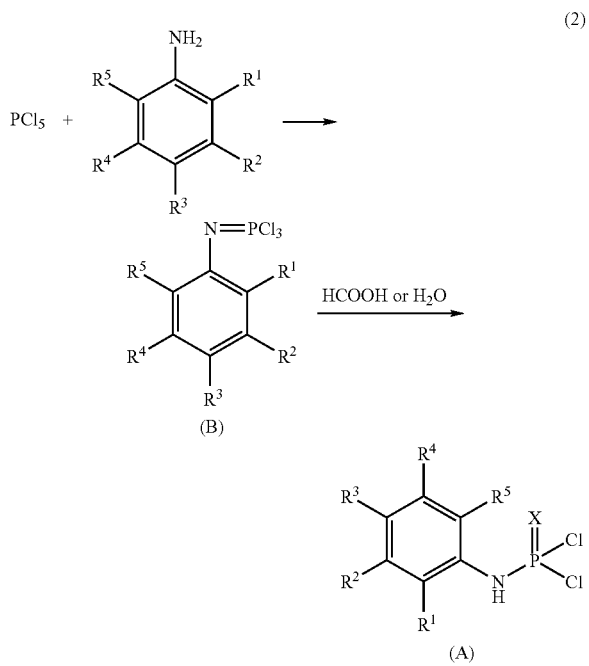

and then b) the type (A) compounds formed in step $a_1$) or $a_2$) are allowed to react with ammonia, if appropriate in an inert organic solvent, at temperatures of from −80 to 30° C. according to equation (3) so as to form the desired end product:

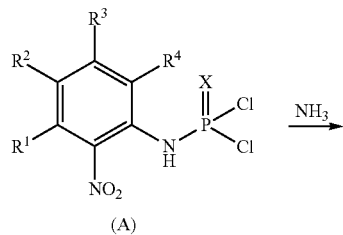

(A)

$\xrightarrow{NH_3}$

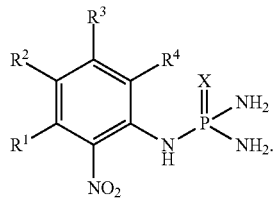

4. A composition containing at least one N-(2-nitrophenyl) phosphoric acid triamide according to claim 1 in a quantity sufficient for urease inhibition and, if appropriate, agriculturally and/or physiologically acceptable and compatible or desired carrier, diluting or thinning means, excipients and if appropriate further active substances.

5. The composition according to claim 4, wherein at least one nitrification inhibitor is contained as a further active substance in a quantity effective for nitrification inhibition.

6. The composition according to claim 5, wherein the nitrification inhibitor is selected from one or more of the following compounds:

pyrazol derivatives with the general formula (IV), or salts or complex compounds thereof:

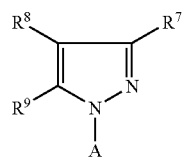

in which
$R^7$, $R^8$, $R^9$ represent, independently of one another, hydrogen, halogen, $C_1$-$C_8$-alkyl, or $C_3$-$C_8$-cycloalkyl and
A the moiety H
or the moiety

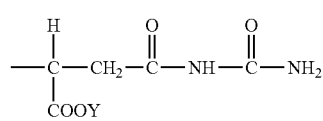

with Y=H, Na, K, $NH_4$ or the moiety
—$CH_2$—B with B=(di)alkylamino

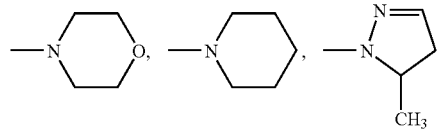

or the moiety

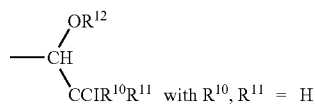

or Cl and

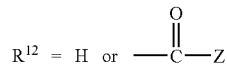

with Z=$C_1$-$C_8$-alkoxy, $C_1$-$C_8$-alkylamino, $C_6$-$C_{10}$-arylamino
or the moiety

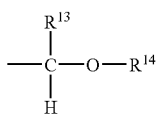

with $R^{13}$, $R^{14}$ = H, $C_1$-$C_8$-alkyl, $C_7$-$C_{18}$-alkylaryl, $C_6$-$C_{10}$-aryl or the moieties

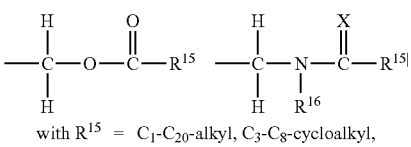

with $R^{15}$ = $C_1$-$C_{20}$-alkyl, $C_3$-$C_8$-cycloalkyl, $C_6$-$C_{10}$-aryl or alkylaryl from $C_1$-$C_4$-alkyl and $C_6$-$C_{10}$-aryl groups; with X=oxygen or sulphur and $R^{16}$ = $C_1$-$C_4$-alkyl, $C_3$-$C_8$-cycloalkyl, $C_6$-$C_{10}$-aryl or H,
wherein the alkyl and aryl moieties listed can be substituted with themselves or by $C_1$-$C_4$-alkylsulfonyl, $C_1$-$C_4$-alkoxy, $C_1$-$C_4$-acyl, halogen, hydroxyl, trimethylsilyl, amino, nitro, sulfo, cyano, carbonyl, carboxyl or $C_1$-$C_5$-carboxyalkyl, 1H-1,2,4-triazoles or their salts or complex compounds, dicyandiamide.

7. A fertilizer composition comprising at least one N-(2-nitrophenyl)phosphoric acid triamide according to claim 1 and optionally at least one member selected from the group consisting of urea-based mineral, organic fertilizer and nitrification inhibitor each in a quantity sufficient for urease inhibition or nitrification inhibition.

8. The fertilizer composition according to claim 7, where at least one N-(2-nitrophenyl)phosphoric acid triamide is contained in a quantity of from 0.001 to 10% by weight in relation to the weight of the urea-based fertilizer.

9. The fertilizer composition according to claim 7, wherein at least one of the nitrification inhibitors is contained in a quantity of from 0.01 to 10% by weight, in relation to the weight of the urea-based fertilizer.

10. A method for extracorporal regulation and inhibition of urease-catalysed urea hydrolysis, comprising applying a N-(2-nitrophenyl)phosphoric acid triamide defined in claim 1 to a locus in need thereof.

11. A method for reducing the nitrogen losses when fertilising with fertilizer urea or urea-based fertilizers, comprising applying a N-(2-nitrophenyl)phosphoric acid triamide according to claim 1 to a locus in need thereof.

12. A method for reducing the ammonia presence resulting from the dung or animal excrement in animal enclosures, comprising applying a N-(2-nitrophenyl)phosphoric acid triamide according to claim 1 to a locus in need thereof.

13. A method for avoiding toxic effects when feeding with feed urea within the framework of animal nutrition, the method comprising applying a N-(2-nitrophenyl)phosphoric acid triamide according to claim 1 for avoiding toxic effects when feeding with feed urea within the framework of animal nutrition.

14. A method for stabilizing urea-based fertilizers that have already been applied or are still to be applied by means of subsequent or previous application, comprising, applying a N-(2-nitrophenyl)phosphoric acid triamide according to claim 1 to a locus in need thereof.

15. A method for fertigation, comprising applying the compositions according to claim 4 to a locus in need thereof.

16. A method for treating a dysfunction or disease selected from the group consisting of catheter encrustation, inflamed and ulcerous stomach and bowel diseases, urolithiasis, pyelonephritis, nephrolithiasis, ammonia encephalopathy, hepatic encephalopathy, hepatic coma, infections of the urinary passage and gastrointestinal infections, comprising administering an N-(2-nitrophenyl)phosphoric acid triamide according to claim 1 to a mammal in need thereof.

17. The method of claim 16, wherein the gastrointestinal infection is caused by helicobacter pylori.

* * * * *